US005879345A

United States Patent [19]

Aneas

[11] Patent Number: 5,879,345

[45] Date of Patent: Mar. 9, 1999

[54] DEVICE FOR CONNECTION WITH A CLOSED CONTAINER

[75] Inventor: Antoine Aneas, Menetrol, France

[73] Assignee: Biodome, Issoire, France

[21] Appl. No.: 836,347

[22] PCT Filed: Sep. 11, 1996

[86] PCT No.: PCT/FR96/01399

§ 371 Date: May 12, 1997

§ 102(e) Date: May 12, 1997

[87] PCT Pub. No.: WO97/10156

PCT Pub. Date: Mar. 20, 1997

[30] Foreign Application Priority Data

Sep. 11, 1995 [FR] France .................................. 95 10787

[51] Int. Cl.$^{6}$ ............................ A61B 19/00; A61M 5/32

[52] U.S. Cl. .......................... 604/411; 215/277; 604/413

[58] Field of Search .................................. 215/251, 254, 215/272, 273, 277; 403/411, 412, 413, 403

[56] References Cited

U.S. PATENT DOCUMENTS 4,251,003 2/1981 Bodenmann .
4,624,667 11/1986 Rutnarak .

FOREIGN PATENT DOCUMENTS

A-1 120 641 7/1956 France .
A-28 54 834 7/1980 Germany .
WO 90/03536 4/1990 WIPO .

*Primary Examiner*—John G. Weiss
*Assistant Examiner*—Ki Yong O
*Attorney, Agent, or Firm*—Oliff & Berridge PLC

[57] ABSTRACT

Device (1) for sealing a closed container (2) comprising a neck (3), the opening (3*a*) of which is plugged, and provided with an external annular lip (3*b*), the device firstly comprising an internal cap (5) for fitting coaxially over the neck (3) of the plugged container (2), comprising catching teeth (6) distributed angularly about the axis (7) of the cap, each teeth having a radially outwards elasticity starting from a position (FIG. 3) of snap-fastening under the annular lip (3*b*), secondly, means (9) of access, which are arranged on the cap (5), and thirdly, an external sleeve (10) for sliding coaxially against and on the outside of the catching teeth (6), including a circumferentially continuous band (10*a*) provided along one of its edges with an internal annular ridge which may be continuous or discontinuous, for snap-fastening under the rim (6*a*), when the said sleeve (10) is in the fitted position. The band is radially elastic so that it can be fitted onto the cap when the annular ridge (11) is in the snap-fastened position, but strong so as to be indivisible, unless the said sleeve (10) is permanently destroyed.

10 Claims, 2 Drawing Sheets

DEVICE FOR CONNECTION WITH A CLOSED CONTAINER

BACKGROUND OF THE INVENTION

The present invention relates to connection with a closed container comprising a neck, the opening of which is plugged by a stopper made of a relatively soft material, for example made of elastomer, and provided with an external annular lip, the said rigid container being, for example, made of glass. As a non-exclusive preference, this connection is used to provide communication between, on the one hand, the aforementioned closed container and, on the other hand, another closed container comprising an end piece, the opening of which is also plugged by a stopper made of a relatively soft and elastic material. This definition applies to various applications among which is included therapy or the administration of a medicinal product, in which case the closed container contains, for example, an active ingredient in the form of a powder, and the other container consists of a flexible pouch containing a liquid medium which can dissolve the powder or active ingredient of the container or place it in suspension, this all being in order to obtain a medicinal preparation in liquid form ready to be administered to the patient.

A connection device, or connector, intended to be assembled in a leaktight manner, on the one hand, with a closed container as previously described, comprising tearable or puncturable tamperproofing means keeping the stopper sterile and, on the other hand, with another container as previously described, itself also comprising tearable or puncturable tamperproofing means keeping the stopper present in the opening of the end fitting sterile without having to remove the tamperproofing means of the two containers to be connected, is described and proposed in accordance with the document WO-9003536.

This connection device comprises:

- a cap intended to fit coaxially over the neck of the container plugged with the stopper, and also covered around the annular lip by the tamperproofing means covering and sealing the whole of the external part of the stopper; this cap is also designed to be fitted over the neck 3 and for this purpose has radially outward elasticity so that it can snap-fasten, by means of an internal annular ridge, under the annular lip of the neck of the container; moreover, this cap comprises a coaxial collar lengthening it and forming an internal bore, which will be dealt with later,
- a transverse element made of a flexible and elastic elastomeric material, attached to and arranged inside the cap, including a transverse wall designed to come into contact with the external part of the stopper; this transverse element comprises an axial end piece or sleeve tube fitted in a leaktight manner over the perforating end of the needle which will be dealt with later, this sleeve tube being closed and perforable at its end sealing the needle,
- means for connecting with the inside of the container, through the stopper, comprising a piston mounted so that it can slide in the bore of the collar of the cap, and a central needle passing through the said piston and including the aforementioned perforating end, capped inside the sleeve tube or end piece of the transverse element made of elastomer.

Such a device is not designed or suited to providing tamperproofing of the container with its stopper, because this tamperproofing is obtained by other means already present on the container. In particular, this device can be fitted and removed at will, relative to the plugged container.

Further, this device provides only temporary sealing, at the moment of connection, with each of the two containers in direct contact with their own sealing means.

A device for connection with a closed container, as previously defined, and completely closing this container, but without tamperproofing it in the sense that it is not put in place permanently on the container is described in accordance with the document U.S. Pat. No. C4624667.

This device interacts with a specific, non-standardized container which can be distinguished from the one described earlier by the presence of an annular rim running round the outside of the external annular lip and forming a housing for a flat, which is also annular, belonging to the stopper which in this case has a specific special shape.

The connection device proper comprises:

- an axial and exterior sleeve tube which is of a single piece with the stopper made of elastomeric material, at its blind end forming a membrane which can be perforated by the central needle
- means for connection with the inside of the container, these consisting solely of a central or axial needle held in the aforementioned sleeve tube by its perforating end,
- a tubular cap sealed by a rim to the annular rim of the neck of the container,
- a protecting means or lid, lengthening the cap coaxially by use of a manual separation means, such as a circumferential line of weakness of the plastic, the lid and the cap together being arranged to cover the needle of the connection means, and especially its other perforating end, coaxially.

The cap previously described, of a single piece with the lid, does not fulfil a tamperproofing function in the sense that these elements may be detached from the annular lip of the container either deliberately or accidentally then put in place and bonded, for example, to this same lip, in which case the user has no visible indication or sign that the connection device has been tampered with, and particularly that the sterile conditions, in the case of the connection device being used in pharmacy or in therapy has been broken.

SUMMARY OF THE INVENTION

The subject of the present invention is a connection device which is effectively tamperproof, and in addition provides effective and permanent sealing of the internal parts both during storage and use of the container, and does so in a simple manner. The objective of this sealing in particular is to preserve both the perforating end of the needle of the connection means and the exterior part of the stopper lying inside the latter within the cap from any external contamination, particularly a break in the sterility of the container, irrespective of the conditions in which the connection device is used or stored.

In accordance with the invention, the following means work together towards this objective:

- first of all, the cap is designed to fit directly over the neck of the container, and come into contact with its wall,
- the transverse wall of the cap is made of a relatively hard material so that it comes directly to rest against the external part of the stopper, and it has a central opening for the passage of the needle from its disconnected position to its connected position, perforating the stopper,
- in addition, an external sleeve is provided which is designed to slide coaxially between and outside of the internal cap, having a circumferential continuous band, provided along one of its edges with an internal annular ridge for snap-fastening under the free rim of the internal cap; this band is sufficiently radially elastic to fit tightly against the internal cap and clamp the latter and snap-fasten by means of the annular ridge under the free edge of the internal cap, but strong enough to be indivisible, unless there is a desire to destroy it.

a means for protecting the connection means from the outside is also provided, in leaktight contact with the collar of the cap.

All of this culminates in the volume lying between the piston of the connection means, the inside of the collar and the exterior part of the stopper delimited by this cap being placed in a state of permanent leak-tightness which is maintained over time unless the connection device is destroyed, this being achieved under conditions which make the connection device tamperproof. This result is obtained, in particular, by simplifying construction of the connection device because the latter in particular has no axial or central elements attached inside the internal cap for protecting the perforating end of the needle.

"Tamperproofing" or "tamperproof" is understood to be the characteristic or result by means of which the connection device cannot be dismantled and/or access to the inside of the container or to the product contained in the latter cannot be had without leaving a sign or indication of this access which is durable, visible or detectable by the subsequent user of the container. In the present case, this sign or indication consists in the partial or complete destruction of the integrity of the container and/or of the connection device.

As regards a container containing a medicinal product, for example, by virtue of the invention, on the one hand, the sterility within the connection device cannot be broken without tampering with the device and/or the container and, on the other hand, any relative movement between the various parts or components of the connection device is practically precluded or is in any case not sufficient to break this seal.

"Leaktightness" or "seal" is understood to be the absence of the passage of any liquid, particularly a contaminated or non-sterile one, from the outside towards the inside of the connection device, and/or contact of the stopper, during the normal conditions of use, handling or storage of the container, of course.

The way in which the technical features defined earlier work together also afford additional advantages.

first of all, it makes it possible to make maximum use of the inherent viscoelastic properties of the stopper, in terms of sealing, both with respect to the outside and with respect to the inside of the container.

the means of the invention also make it possible to get away with relatively high tolerances both on the stopper in terms of thickness and on the annular lip of the container, also in terms of thickness, which means that when the aforementioned tolerances are at a maximum, the inside of the connection device remains sealed to the outside.

the connection device remains compatible with all standard containers as used particularly in pharmacy, and in accordance with the standards ISO4362-3 or ISO8362-1, the user has no visible or external means available which would allow him easily to force or to tamper with the connection device once the latter has been fitted permanently on the closed container.

and this device can easily be fitted on the already-closed container without, in particular, modifying the lines or equipment used for packaging the product contained in the said container.

BRIEF DESCRIPTION OF THE DRAWINGS

The present invention is now described with reference to the attached drawing in which.

DETAILED DESCRIPTION OF PREFERRED EMBODIMENTS

Figures 1, 2, 3:
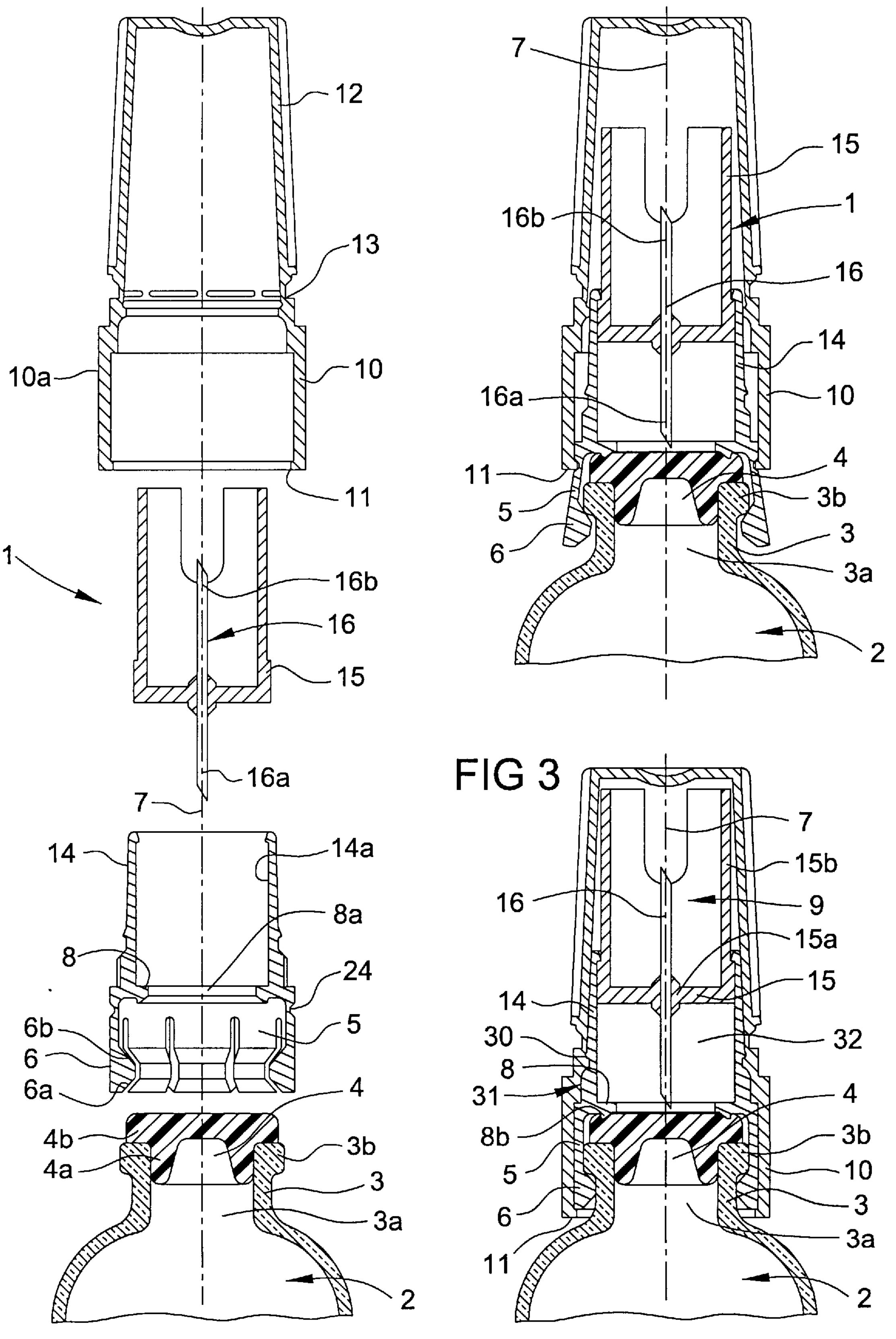
FIG. 1 represents, as an exploded view, a connection device in accordance with the invention in relation to the stoppered or closed container for which it is intended.
FIG. 2 represents one step in the fitting of the connection device according to FIG. 1, during which step the external sleeve is temporarily fitted over the internal cap, the latter being snap-fastened under the neck of the container.
FIG. 3 represents the connection device according to FIG. 1, permanently fitted on the stoppered container.

A device 1 according to the present invention has a dual function. On the one hand, it tamperproofs a container 2, for example a glass bottle, containing a product, not represented, and which has previously been closed or stoppered; this may, for example, be a conventional bottle containing a medicinal product in the form of a powder, closed or stoppered, as it leaves the production line or equipment for packaging this same medicinal product. In use, it also allows a sealed connection to be provided or set up between the inside of the container 2, on the one hand, and the inside of another vessel (not represented) on the other hand, for example a flexible pouch containing a liquid in which the aforementioned medicinal product is intended to be dissolved or suspended. The result of this is that the container 2 does not have its own tamperproofing means.

This bottle 2 includes a neck 3, the opening 3*a* of which is plugged by a stopper 4, in a sealed manner. This stopper 4 is made of a relatively soft material, for example an elastomer such as rubber. The neck 3 around its opening 3*a* has an external annular lip 3*b* serving, as described below, for fitting and fixing the connection device according to the invention. The stopper 4 has a cylindrical central part 4*a* designed for being fitted flexibly and in a sealed manner inside the neck 3, and a flattened external part 4*b* which lies against the annular lip 3*b*.

A connection device according to the invention essentially comprises:

an internal cap 5 designed to fit coaxially over and fix onto the neck 3 of the container 2, plugged with the stopper 4, means 9 for connection with the inside of the container 2, through the stopper 4, these means being arranged and interacting with the internal cap 5, an external sleeve 10 designed to slide coaxially against and on the outside of the internal cap 5, and to fit permanently over the latter, tightly gripping the cap 5, a protection means or lid 12 for the connection means 9, fitted on the external sleeve 10.

The internal cap 5 and the external sleeve 10 are each made as a single piece of a plastic, or of a material which is relatively hard, by comparison with the material of the stopper 4 which is relatively soft. In particular, the external sleeve 10 is made of a plastic having a relatively high elastic modulus, for example a technical-grade plastic such as a polyamide or a high-density polyethylene, while the internal cap is made of a plastic which has a lower elastic modulus, for example a low-density polyethylene.

The internal cap 5 comprises catching teeth 6, separated from one another and distributed angularly about the axis 7 of the cap, which is the axis of the connection device 1, and together forming a skirt of cylindrical shape. Each tooth 6 has elasticity radially outwards so that it can snap-fasten (cf. FIG. 3) under the annular lip 3*b* of the neck 3.

As represented in FIG. 1, the catching teeth 6, and therefore the cylindrical skirt which they form, therefore have a normal position, that is to say a position which is not stressed radially outwards, which corresponds to direct contact with the neck 3 and underneath the annular lip 3*b*. However, they have elasticity radially outwards pulling them back centripetally towards the neck 3, and allowing them to negotiate the flattened external part 4*b* of the stopper 4 and the annular lip 3*b* of the stopper 4 when the internal cap 5 is pushed down over the neck 3 of the container.

Each catching tooth 6 has an internal heel 6*b* with a shape designed to interact with the lower rim of the annular lip 3*b*. The internal cap 5 also includes, as a single piece with the catching teeth 6, a relatively rigid transverse wall 8 for resting against the flat external part 4*b* of the relatively soft stopper 4. A central opening 8*a* is made in the wall 8 in relation to the connection means 9 described later. This central opening 8*a* forms, with the rest of the internal cap 5, an annular flank for resting against the flattened external part 4*b*, of the stopper 4. This annular flank has a circumferential and continuous rib 8*b* on the stopper 4 side, intended at least partially to penetrate the relatively soft material of the stopper 4.

The external sleeve 10 is designed to slide coaxially against and on the outside of the skirt formed by the catching teeth 6 of the internal cap 5. This external sleeve 10 has a circumferentially continuous band 10*a* provided along one of its edges, namely its free edge, with an internal annular ridge 11 which may be continuous or discontinuous for snap-fastening under the free rim 6*a* of the internal cap 5 or, more specifically, of its catching teeth 6. As represented in FIG. 3, once the external sleeve 10 is permanently fitted on the internal cap 5, with the internal annular ridge 11 snap-fastened under the catching teeth 6, the latter are protected and are no longer visible or accessible from the outside. This band 10*a*, for example made of plastic, is radially elastic enough to be fitted tightly over the internal cap 5, gripping the latter tightly towards the position in which the annular ridge 11 is snap-fastened, but strong enough to be indivisible, unless the external sleeve 10 and therefore the band 10*a* is permanently destroyed. The consequence of this is that when the external sleeve 10 is in its position fitted onto the internal cap 5, the band 10*a* radially grips the catching teeth and the corresponding skirt centripetally against the neck 3 of the container 2, which is itself strong and rigid, because it is made of glass, for example. As stated earlier, the external sleeve 10, and in particular the band 10*a*, are made of a material which has good mechanical properties, so that they are continuous and have no line or region of weakness as regards the band 10*a*, which gives the latter the properties of being tear-proof and indivisible, unless of course the band 10*a* is permanently destroyed, for example using a cutting tool or instrument.

The protecting means or lid 12 is fitted on the external sleeve 10, at the opposite end from the internal annular ridge 11, with the use of a means 13 for manually separating the lid from the sleeve 10. As a non-exclusive preference, the lid 12 and the external sleeve 10 are constructed as a single piece made of plastic with a perforated circumferential ring of weakness separating them, and forming the means 13 of manual separation defined earlier. The protecting means or lid 12 is fitted in sealed contact on the outside and with the collar 14 described later, forming part of the connection means 9. This sealed contact, especially sealed against any liquid, is obtained using any appropriate means known per se, for example using stepped circumferential slender strips obtained directly by moulding on the outside of the collar 14 and engaged with the internal bearing surface of the lid 12.

Means 30 for preventing translational movement are arranged between the external sleeve 10 and the collar 14 of the cap 5 so that they complement the internal annular ridge 11 in the position in which the external sleeve 10 is fitted over the internal cap 5. These means consist of a circumferential rib projecting inside the internal sleeve 10 and a corresponding circumferential groove formed around the outside of the collar 14. All of this, together with the internal annular ridge 11 allows the external sleeve 10 to be immobilized permanently in terms of translation on the internal cap 5.

Means 31 for preventing rotational movement are arranged between the external sleeve 10 and the internal cap 5, when the external sleeve 10 is in its position fitted on the cap. These means, which have not been represented, include for example internal longitudinal ribs on the external sleeve 10 interacting with corresponding suitable external longitudinal grooves made on the collar 14. These arrangements make it possible to block the external sleeve 10 in terms of rotation in its position fitted on the internal cap 5, which makes it possible to avoid digging into the stopper 4 or forming therein a depression which would be detrimental to sealing, in register with the rib 8*b*.

To make the assembly of the connection device, followed by its permanent fitting on the closed container easier to perform automatically, the internal cap 5 includes or defines a slot 24 designed to take the internal annular ridge 11 of the external sleeve 10 and allow temporary and coaxial assembly of the cap 5 and of the sleeve 10.

Figure 4:
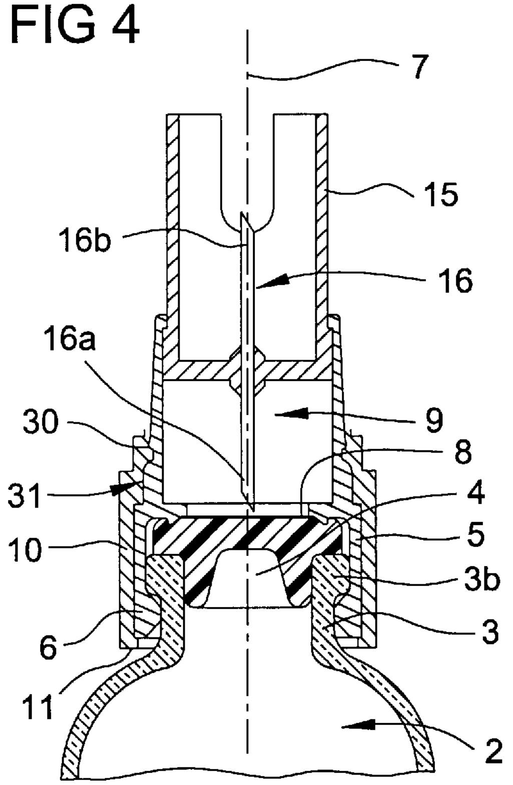
FIG. 4 represents the container with its connection device from which a lid has been removed.

The connection means comprise, on the one hand, a collar 14 lengthening the internal cap 5 in a one-piece and coaxial manner and forming an internal bore 14*a* and, on the other hand, a piston 15 mounted so that it can slide in the bore 14*a* between a disconnected position represented in FIGS. 3 and 4, in which the piston is at the opposite end to and some distance away from the stopper 4, and a connected position, not represented, in which the piston 15 is arranged on the same side and against the stopper 4, and its flattened exterior part 4*b*. A central or coaxial needle 16 passes through the piston 15 and has one end 16*a* for perforating the stopper 4 and another end 16*b* for connection, for example, with another container, especially a flexible pouch for a liquid for example. This needle 16 is made of metal or of plastic with one or two flow ducts. The connection end 16*a* and/or 16*b* is possibly designed to avoid the loosing of particles or fragments resulting from the perforating of the stopper 4. As shown by FIGS. 2 and 3, the lid 12 and the internal cap 5 are designed one with respect to the other to contain the connection means 9 in their position disconnected from the inside of the container 2, that is to say with the piston 15 arranged some distance from the stopper 4, without any penetration of the perforating end 16*a* of the needle 16 in the said stopper.

In the configuration of the device according to the present invention as represented in FIG. 3, ready for use and tamperproof, the internal bore 14*a* of the collar 14, the piston 15 in its position some distance away from the stopper 4, the external face thereof bounded by the annular flank of the transverse wall 8*a* of the internal cap 5 together delimit a chamber 32 in which the end 16*a* of the needle 16 is arranged without any special protection, especially perforable flexible end piece. This end 16*a* is therefore directly facing the stopper 4. The sealing of this chamber 32 to external fluids is provided, on each side of the collar 14, by the lid 12 mounted in a sealed manner on the collar 14, and by the hard/soft bearing of the transverse wall 8, particularly of the rib 8*b* which partially penetrates the stopper 4. This seal makes it possible, through the time that the container 2 is stored with the device according to the invention, to maintain the sterile conditions within the chamber 32, and in particular of the external surface of the stopper 4 and of the perforating end 16*b* which when the connection means 9 are activated will come into contact with one another.

As represented in the figures, the piston 15 comprises a transverse web through which the needle 16 passes, and an external sleeve tube 15*b* opposite the stopper 4 which guides any end piece of another container, for example a pouch of fluid with which the inside of the container 2 is connected.

The assembly followed by the fitting of the connection device 1 previously described on the container 2 takes place, especially in an automatic fashion, as follows:

- the piston 15 with the needle 16 is arranged and fitted in the "up" position inside the bore 14*a* of the collar 14, of a single piece with the internal cap 5;
- the external sleeve 10, of a single piece with the lid 12 is temporarily fitted on the internal cap 5 using the annular ridge 11 snap-fastened in the groove 14 of the internal cap 5;
- the connection device 1, thus temporarily fitted is snap-fastened under the annular lip 3*b* of the container 2, using the catching teeth 6 of the cap;
- under continuing axial thrust on the lid 12, the band 10*a* of the sleeve 10 fits permanently and tightly on and around the skirt formed by the external parts of the teeth 6 with the annular ridge 11 snap-fastened under the rim 6*a* of the cap 5 (cf. FIG. 3).

From this moment, the container 2 is rendered tamperproof because the internal cap 5 can be detached from the container 2 only by breaking and therefore destroying the band 10*a*, without the user having the possibility of reconstructing the sealing device 1. In this permanent configuration, the inside of the collar 14 is permanently isolated from the outside in a sealed manner, particularly with regard to fluids, which in particular makes it possible to preserve its sterility. In particular, small relative movements of the device 1 according to the invention with respect to the container 2 are unable to break this seal.

In this configuration too, the internal cap 5 is fitted directly over the neck 3 of the container, in contact with the glass, without the interposition of any other tamperproofing means such as a tearable metal or plastic collar. The same is true of the transverse wall 8 of the internal cap 5 which rests directly against the external part of the stopper 4.

At the time of the first use, by separating the lid 12 from the sleeve 10 along the dividing line 13, in accordance with FIG. 4, the container 2 is ready for use, on account of the accessibility of the connection means 9, which in particular can then be activated into it connected position by pushing the piston 15 down towards the stopper 4, inserting the end 16*b* of the needle 16 in the end piece of some other container or pouch.

Various tests conducted with a connection device according to the invention and as described earlier have shown that this device remained sealed and constituted an effective microbe-proof barrier against any external contamination.

What is claimed is:

1. Device for connection to a closed container, said container comprising a neck an opening of said neck being plugged by a stopper made of relatively soft material, and provided with an external annular lip, the connection device comprising:

- a cap designed to fit coaxially over the neck of the container plugged with the stopper, elastic radially outwards so that it can snap-fasten over the annular lip of the neck, the cap comprising a coaxial collar lengthening it and forming an internal bore,
- a transverse wall for coming into contact with an external part of the stopper, and
- means for connection with the inside of the container through the stopper, comprising a piston mounted so that it can slide in a bore of the collar of the cap, a central needle passing through the piston and having one end for perforating the stopper,
- wherein in combination, the cap is designed to fit directly over the neck of the container, the transverse wall is made of a relatively hard material for coming directly to bear against the external part of the stopper and includes a central opening for the passage of the central needle of the connection means, and the device furthermore includes, on the one hand, an external sleeve designed to slide coaxially against and on the outside of the internal cap, including a circumferentially continuous band provided along one of its edges with an internal annular ridge for snap-fastening under a free rim of the internal cap which is radially elastic enough to fit tightly against the internal cap and snap-fasten by means of the annular ridge under the free edge but is strong enough to be indivisible and means for protecting the connection means from the outside, in leaktight contact with the collar of the cap.

2. Device according to claim 1, wherein the transverse wall is constructed as a single piece, made of plastic, with the internal cap.

3. Device according to claim 1, wherein the transverse wall comprises a continuous circumferential rib intended to penetrate, at least partially, the relatively soft material of the stopper.

4. Device according to claim 1, further comprising means for preventing translational movement arranged between the external sleeve and the collar of the cap, said means complementing the internal annular ridge in a position where the external sleeve is fitted tightly on the internal cap.

5. Device according to claim 1, further comprising means for preventing rotational movement arranged between the external sleeve and the internal cap in a position where the external sleeve is fitted tightly on the internal cap.

6. Device according to claim 1, wherein the internal cap comprises catching teeth distributed angularly about an axis of the cap, each tooth having elasticity radially outwards so that it can come into a position where it is snap-fastened under the annular lip of the neck.

7. Device according to claim 1, wherein the protection means includes a lid fitted over the external sleeve and means for manually separating the lid from the sleeve.

8. Device according to claim 7, wherein the lid and the external sleeve are constructed as a single piece made of plastic, with a perforated circumferential ring of weakness separating them and forming the means for manual separation.

9. Device according to claim 1, wherein the central needle has another end for connecting with another container.

10. Ready-for-use assembly comprising a closed container containing a product, said container including a neck, the opening of which is plugged by a stopper made of relatively soft material and provided with an external annular lip, and a connection device according to claim 1, mounted permanently on said container, by means of the external sleeve being fitted tightly over the internal cap, itself snap-fastened under the annular lip of the container.

* * * * *